US007058438B2

(12) United States Patent
Grace et al.

(10) Patent No.: US 7,058,438 B2
(45) Date of Patent: Jun. 6, 2006

(54) METHOD AND APPARATUS FOR SELF-DIAGNOSTIC EVALUATION OF NERVE SENSORY LATENCY

(76) Inventors: Lawrence J. Grace, 50 Donna La., Hollister, CA (US) 95023; Richard J. Enroth, 1120 Jacqueline Dr., Hollister, CA (US) 95023

( * ) Notice: Subject to any disclaimer, the term of this patent is extended or adjusted under 35 U.S.C. 154(b) by 145 days.

(21) Appl. No.: 10/405,917

(22) Filed: Apr. 1, 2003

(65) Prior Publication Data

US 2004/0024299 A1 Feb. 5, 2004

Related U.S. Application Data

(63) Continuation of application No. 09/706,455, filed on Nov. 2, 2000, now Pat. No. 6,553,245.

(51) Int. Cl.
*A61B 5/04* (2006.01)
*A61B 5/05* (2006.01)

(52) U.S. Cl. ...................... 600/375; 600/372; 600/382; 600/384; 600/386; 600/546; 600/547; 600/554

(58) Field of Classification Search ................ 600/375, 600/372, 382, 384, 386, 546, 547, 554
See application file for complete search history.

(56) References Cited

U.S. PATENT DOCUMENTS 3,364,929 A * 1/1968 Ide et al. .................... 600/554
3,785,368 A * 1/1974 McCarthy et al. .......... 600/384
3,898,983 A * 8/1975 Elam .......................... 600/554
4,291,705 A * 9/1981 Severinghaus et al. ..... 600/546
4,805,636 A * 2/1989 Barry et al. ................ 600/586
4,807,643 A * 2/1989 Rosier ........................ 600/554
4,811,742 A * 3/1989 Hassel et al. ............... 600/546
5,050,612 A * 9/1991 Matsumura ................. 600/483
5,131,401 A * 7/1992 Westenskow et al. ....... 600/554
5,215,100 A * 6/1993 Spitz et al. ................. 600/554
5,300,096 A * 4/1994 Hall et al. ..................... 607/48
5,327,902 A * 7/1994 Lemmen ..................... 600/547
5,333,618 A * 8/1994 Lekhtman et al. .......... 600/547
5,540,735 A * 7/1996 Wingrove .................... 607/46
5,752,512 A * 5/1998 Gozani ....................... 600/347
5,771,891 A * 6/1998 Gozani ....................... 600/347
5,797,854 A * 8/1998 Hedgecock ................. 600/554
6,151,519 A * 11/2000 Sugihara et al. ........... 600/372
6,324,432 B1 * 11/2001 Rigaux et al. ................ 607/62
6,540,673 B1 * 4/2003 Gopinathan et al. ........ 600/300
6,553,245 B1 * 4/2003 Grace et al. ................ 600/375

OTHER PUBLICATIONS

Baker, A.B. et al. (eds.); "Clinical Neurology," Cover page, vol. 4, Chapter 51, pp. 41 thru 43, Harper & Row, Philadelphia, Revised Edition (1983).

* cited by examiner

*Primary Examiner*—Henry Bennett
*Assistant Examiner*—Nihir Patel
(74) *Attorney, Agent, or Firm*—John P. O'Banion

(57) ABSTRACT

A portable apparatus which allows a user to perform self-diagnostic evaluation of nerve sensory latency between a pair of epidermal locations proximal to nerve conduction paths. The device provides a simple and low-cost self-diagnostic apparatus which may be used for the detection and ongoing monitoring of sensory latency, such as sensory latency which is the result of carpal tunnel syndrome. The apparatus is powered by a single battery which provides power to all circuitry of the apparatus. Upon power activation, the device generates a series of high voltage stimulus pulses at an electrode in epidermal contact with the user/operator. The nerve response voltage is detected by a second electrode located along nerve pathway and the time delay between stimulus and response is displayed and periodically updated as each new response is detected.

12 Claims, 7 Drawing Sheets

METHOD AND APPARATUS FOR SELF-DIAGNOSTIC EVALUATION OF NERVE SENSORY LATENCY

CROSS-REFERENCE TO RELATED APPLICATIONS

This application is a continuation of U.S. patent application Ser. No. 09/706,455 filed on Nov. 2, 2000, now U.S. Pat. No. 6,553,245, incorporated herein by reference.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

This invention pertains generally to neurological diagnostic techniques, and more particularly to an apparatus for performing self-diagnostic measurements of nerve sensory latency such as may be exhibited as a result of carpal tunnel syndrome.

2. Description of the Background Art

Median nerve compression in the wrist, also called "carpal tunnel syndrome" is becoming an increasingly common disorder that causes pain and suffering, as well as a substantial economic impact. Carpal tunnel syndrome has various causes and predispositions which include genetic, toxic, metabolic and traumatic factors. The leading causes of the disorder stem from cumulative trauma or repetitive motion mechanisms. Primarily, the causative factors are related to the nature of the work performed and the ergonomic environment of the workplace.

Carpal tunnel syndrome has become an agonizing disorder for many sufferers while a far larger segment of the population experiences various levels of discomfort and disability. Concomitant economic costs exist which are more easily quantified as costs for medical treatment, disability payments, insurance premiums, along with the economic impact of decreased worker and industrial productivity.

The current medical industry consensus is that measuring the time required for a sensory nerve action to cross the wrist after the occurrence of a depolarizing incident is the most definitive test available for nerve compression. Since nerve conduction is bi-directional, the stimulus can be applied to a finger and recorded from the nerve above the wrist, or the converse, wherein each method is valid and should provide equivalent results. Measurements on conduction times in healthy individuals which are not experiencing compression of the carpal nerves provide a narrow range of conduction times which are reproducible over extended time periods. A nerve under compression responds with a lower conduction velocity, and thereby a longer conduction period, or latency, between the stimulus and the response. Ranges of normal latency values have become well known with a number of comprehensive case studies to be found in the literature.

Diagnostic testing is currently being performed by professionals, such as neurologists and physiatrists in medical offices, clinics, or in neurophysiology laboratories. Various laboratory and clinical equipment is currently available to allow a medical practitioner to assess patient nerve conduction, however, the expense of purchasing and using these devices has limited their use. The equipment typically being employed by the medical community provides a suite of testing functions and includes a waveform display in addition to a digital readout. A percentage of insurance plans, including Medicare®, require the submission of a waveform graph in order for the test costs to be reimbursed. Presently the fee for performing this test (approximately five hundred dollars per examination) puts the technique out of the range of economic feasibility for many applications.

Due to the cost and limited accessibility of the equipment and practitioners, only a small minority of patients receive the definitive testing, and often by the time the testing is performed, the severity of the nerve compression already warrants surgery. The screening of a larger segment of the population to monitor ongoing sensory nerve conduction of those performing vigorous or repetitive motion activities would be a welcome and valued asset within industry, government, and in the field of ergonomics which endeavors to assess and remediate this major debilitating disorder.

Carpal tunnel syndrome may be caused by a number of factors, of which "occupational neuropathy" is but one of at least twenty five identified causes as described in Baker's Textbook of Clinical Neurology. Other common causes include pregnancy, diabetes, congestive heart failure, arthritis and familial heredity. The screening efforts for carpal tunnel syndrome by professionals and their agents or technicians, has focused on larger organizations with known or suspected risk factors. A large percentage of workers, therefore, are unserved by these screening methods, such as those laboring in small businesses, trades or crafts, services and farms, along with many self-employed workers.

Therefore, a need exists for an inexpensive, easy to operate instrument which provides self-diagnostic screening of nerve latency such as median nerve latency which is exhibited as a result of carpal tunnel syndrome. The present invention satisfies those needs as well as others, and overcomes the deficiencies of previous approaches.

BRIEF SUMMARY OF THE INVENTION

The present invention provides an apparatus for self-diagnosis of nerve sensory latency that is suitable for providing self-diagnostic evaluation of carpal tunnel syndrome. The apparatus provides a series of stimulus pulses at a first electrode while the nerve responses to those stimulus pulses are monitored at a location farther along the nerve path. The apparatus calculates the latency, or delay, from each stimulus to each response, and provides a readout of the latency period. The controls and readout of the apparatus make it ideal for self-diagnostic evaluation of carpal tunnel syndrome as well as other conditions wherein a nerve sensory latency is exhibited.

Once the apparatus is activated, the user is free to position the stimulator probe with their free hand, as they are not required to interact with the apparatus to initiate each stimulus pulse. By way of example, the unit may be connected with a stimulus probe positioned just above the wrist and a recording electrode located on a finger. Unless nerve compression is occurring, the delay between stimulus and response along the nerve should typically be less than three milliseconds. Mechanical pressure on the nerve increases conduction time, and this increase, which is referred to as "prolongation", is proportional to the applied pressure. The apparatus of the present invention provides a portable unit configured to allow for self-diagnostic evaluation. The exemplified unit is designed for wide deployment as it can be manufactured from low cost circuitry. By increasing availability and lowering cost; it is anticipated that periodic evaluation will be made feasible so that early detection and treatment can be provided, perhaps without surgery.

An object of the invention is to provide an apparatus for performing self-diagnostic analysis of sensory nerve latency, such as that exhibited as a result of carpal tunnel syndrome.

Another object of the invention is to provide accurate measurement of prolongation.

Another object of the invention is to provide an easy to use and low cost portable carpal tunnel diagnostic apparatus.

Another object of the invention is to provide a carpal tunnel diagnostic apparatus having low power consumption and the ability to operate from a single battery.

Another object of the invention is to provide a carpal tunnel diagnostic apparatus having an output display that provides unambiguous nerve propagation readings.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Referring more specifically to the drawings, for illustrative purposes the present invention is embodied in the apparatus generally shown in FIG. 1 through FIG. 7. It will be appreciated that the apparatus may vary as to configuration and as to details of the parts, and that the method may vary as to the specific steps and sequence, without departing from the basic concepts as disclosed herein.

Figure 1:
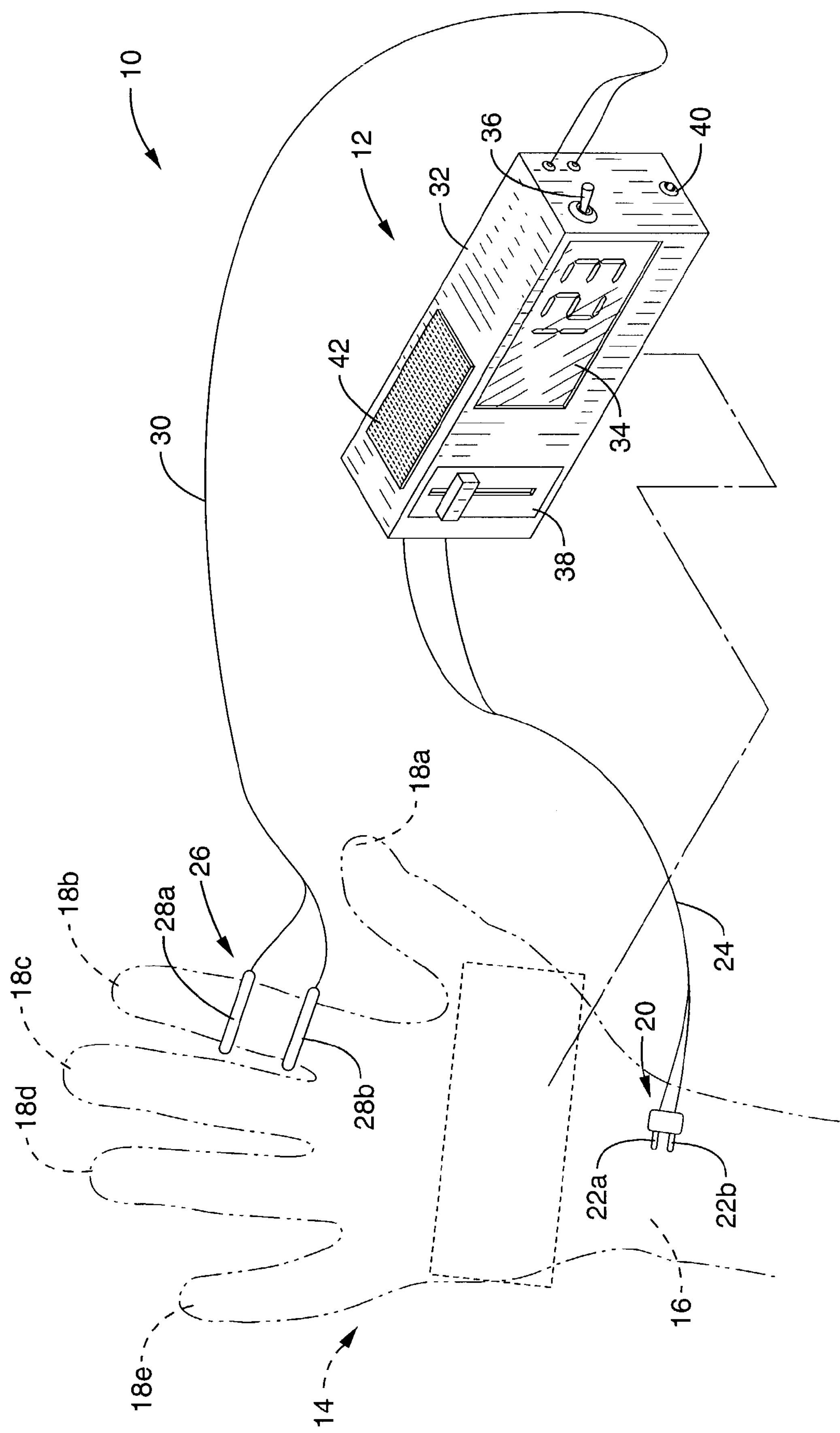
FIG. 1 is a perspective view of a self-diagnostic nerve sensory latency evaluation apparatus according to the present invention shown held in the hand of the user and connected for evaluating median nerve sensory latency.

Referring first to FIG. 1, a self-diagnostic nerve sensory latency apparatus 10 according to the present invention is shown connected to a user for measuring carpal tunnel prolongation. The apparatus 10 is shown with a base unit 12 connected to the hand 14 of a user performing a self-examination. The apparatus is preferably held in the hand 14 of the user to provide beneficial grounding (a neutral), for improved measurement accuracy. The hand 14 (shown in phantom along with intended apparatus positioning) of the user is shown with wrist 16 along with thumb 18*a* and fingers 18*b* through 18*e*. A stimulator probe 20, having electrodes 22*a*, 22*b*, is connected to the base unit 12 by a wiring harness 24. The stimulator electrodes 22*a*, 22*b* are shown positioned in topical proximity with the median nerve on the underside of the wrist (on the middle of the palm side of the wrist). The negative electrode (cathode) 22*a* is shown oriented toward the hand, while the positive electrode (anode) 22*b* is shown oriented toward the forearm. A recording electrode 26 is shown connected on the user's index finger by a pair of rings 28*a*, 28*b*, and is also shown connected to the base unit 12 by a wiring harness 30.

The base unit 12 includes a display 34 upon which the latency readings are registered, a power-on switch 36, and a stimulator amplitude control 38. A snap connection 40 is shown on one end of the unit for the attachment of an optional retention strap or the like which provides improved retention and conduction with the hand of the user. The retention strap for this embodiment (not shown) is preferably configured with a snap proximal to one end for attachment to snap connection 40, and a strip of hook-and-loop fastener, such as Velcro®, to mate with the corresponding hook-and-loop fastener section 42 on the top of base unit 12. Preferably the strap would contain conductive material to further enhance grounding and the user would simply pull the strap around the back of their hand and over onto the hook-and-loop fastener to secure the unit to their hand. It will be appreciated that the added securement provided by the strap can be implemented using a variety of straps or clips configured with any of numerous fastening mechanisms. The connection to the strap may also be utilized should an application arise in which the apparatus can not be hand-held, such as in the case of a post-surgically bandaged hand, wherein the strap may be held to the hand or a longer grounding strap employed to electrically connect the case of the apparatus to the hand of the patient.

It will be appreciated that the apparatus housing may be configured in various shapes to enhance placement within the hand of the user. For example, the apparatus can be constructed of plastic in a variety of smooth cornered shapes wherein the exterior conductivity is achieved by applying metal powder coating, or a similar conductive material, to the exterior of the housing so that advantageous grounding for the apparatus within the hand of the user is provided.

In use, the apparatus is first placed in the hand of the user with the optional strap being fastened if added security is desired. The recording electrode 26 is then attached proximal to a position along a nerve pathway for which the nerve response is to be measured. In the illustrated embodiment, electrode rings 28*a*, 28*b*, (positive and negative, respectively) are shown annularly disposed on the index finger 18*b* of the user. The recording electrode rings may be placed on the index finger, or the middle finger, with the cathode (−) at the base, and the anode (+) approximately an inch toward the tip of the finger. It is beneficial to enhance the electrical contact of the stimulator probe 20 and the recording electrodes 26 with the skin surface. Enhanced conductivity may be accomplished by lightly coating the rings and probes with a conductive paste or gel. Commercial conductive gels are available and numerous simple household items may alternatively be used, such as toothpaste.

Once base unit 12 is activated by switch 36, electrical stimulus pulses travel from base unit 12 through wiring harness 24 to the stimulator probe 20. The stimulator probe 20 is placed proximal to the opposing end of the nerve segment of interest, in this case the median nerve, such that the stimulus pulses are now being transmitted along the median nerve to the recording electrode 26. The amplitude of the stimulus pulses is set by means of amplitude control 38 which is initially adjusted to a low amplitude, or a known amplitude as set from a prior use.

A brief twitch of the muscles at the base of the thumb will occur as the motor nerves are activated. The motor nerve twitching indicates that a proper contact path along the nerve has been established and that the stimulus voltage is sufficiently high, since the threshold for activation of the sensory branch (being evaluated) is lower than the threshold for motor nerves. Users quickly adapt to the unusual sensation of the very brief shock pulses and the associated muscle twitch.

A series of latency measurements are then registered on the display 34 providing the user with diagnostic information about the sensory delay along the particular nerve being evaluated, which in this case is the median nerve. High latency periods exceeding approximately three-milliseconds for the median nerve often are attributable to the compression of the median nerve by the carpal tunnel which is the condition commonly referred to as carpal tunnel syndrome. A reading below three milliseconds covers at least 95% of normal, asymptomatic subjects. The higher reading is even more meaningful if the subject has been experiencing numbness or tingling in the hand or fingers. In view of the simple self-diagnostic procedure and the low cost for the apparatus itself, periodic diagnostic evaluations can be warranted for individuals at-risk of repetitive motion activities or for checking the positive effects of ergonomic interventions designed to mitigate repetitive motion effects. Response to simple treatments such as wrist splinting or bracing may also be evaluated. The latency time recorded by the diagnostic evaluation may vary by a few tenths of a millisecond if the fingers or hand are cool or cold. In such instances the hand may be warmed in water prior to evaluation so that a nominal exterior body temperature is achieved.

Figure 2:
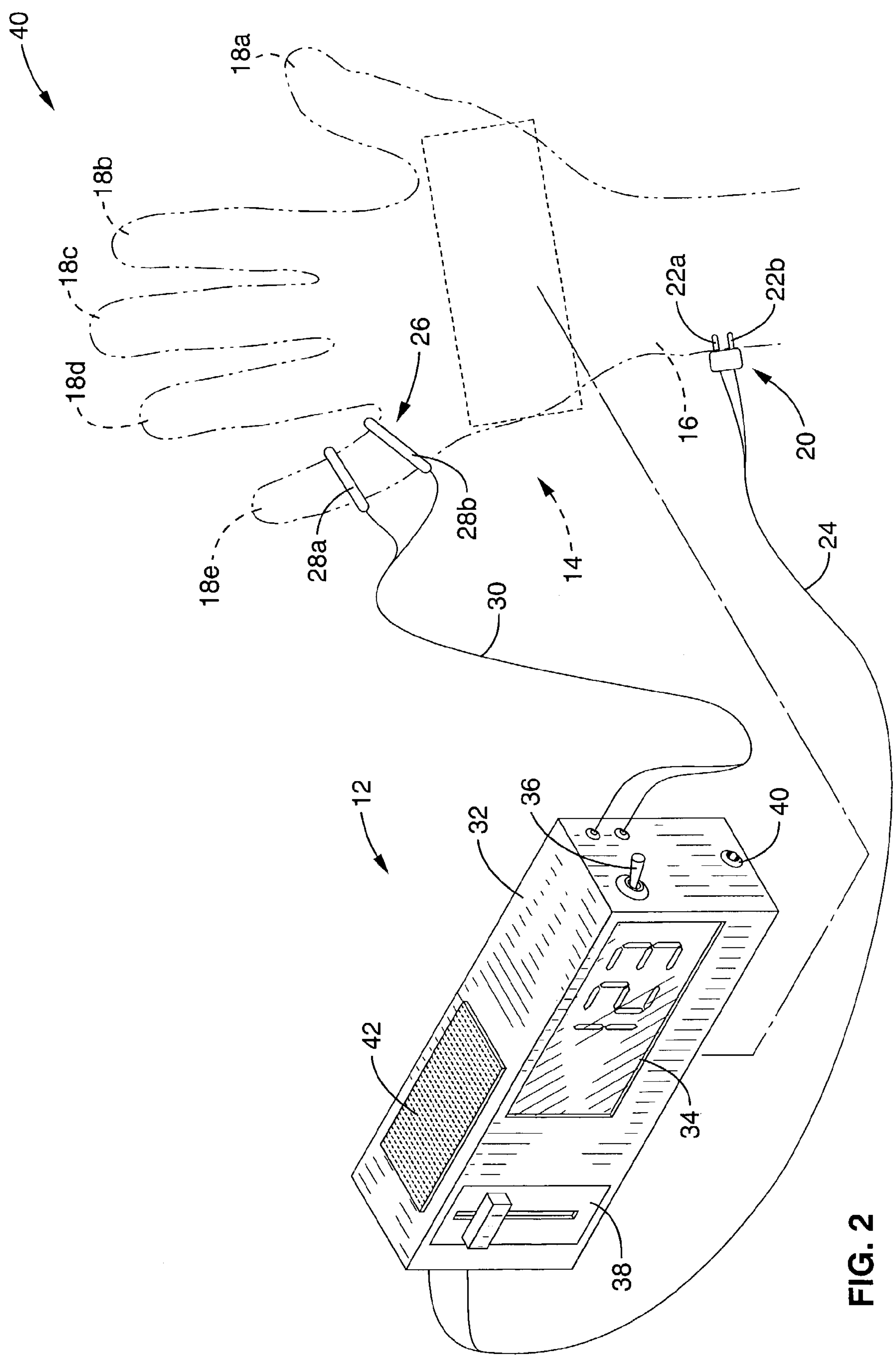
FIG. 2 is a perspective view of a self-diagnostic nerve latency evaluation apparatus according to the present invention shown held in the hand of the user and connected for evaluating ulnar nerve sensory latency.

Referring now to FIG. 2, the user with similar ease may self-diagnose sensory latency of the ulnar nerve along the nerve pathway from above the wrist to the little finger. Here, electrode rings 28*a*, 28*b* are placed on the fifth (small or pinky) finger 18*e* and the stimulator probe 20 is moved proximal to the ulnar nerve on the underside of the wrist. The user may be required to reposition the stimulus probe on the wrist until stable readings are provided on the display 34, so as to properly locate the ulnar nerve pathway. An accompanying muscle twitch is expected to occur in the small muscle bulge (hypothenar), between the fifth finger and the wrist, which is a further indicator of proper stimulus contact with the ulnar nerve. The sensory latency interval along the ulnar nerve is typically less than that for the median nerve due to the shorter anatomical length along the segment of ulnar nerve. The ulnar nerve is not carried through the carpal tunnel of the wrist, and as a result prolongation is not exhibited by the ulnar nerve in response to carpal tunnel syndrome. Therefore, if the median nerve sensory latency of the user exceeds the ulnar latency by more than approximately one millisecond, then this provides definitive evidence that the median nerve of the patient is being compressed and that the user has carpal tunnel syndrome.

Figure 3:
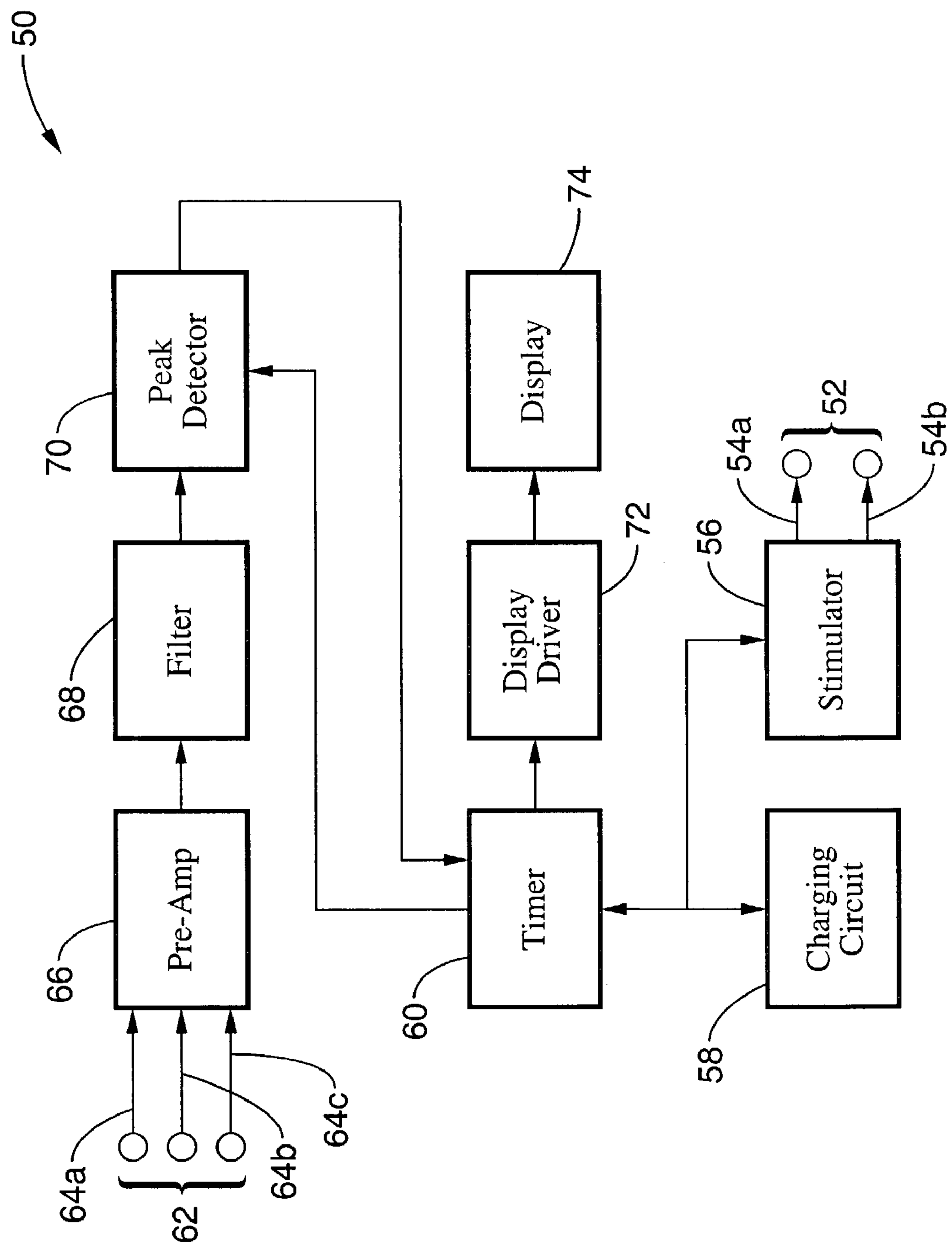
FIG. 3 is a block diagram of the self-diagnostic nerve latency evaluation apparatus according to the present invention.

FIG. 3 is a representative block diagram 50 for the electronic circuitry for the embodied self-diagnostic nerve sensory latency evaluation apparatus. The output 52 of the apparatus comprises a pair of electrode outputs 54*a*, 54*b* from the stimulator circuit 56 to which wiring harness 24 (and electrodes 22*a*, 22*b*) is connected. The pulse voltage generated between the positive and negative electrodes stimulate the nerves in the nearby nerve pathway such that the nerve response travels along the pathway and is sensed by the recording electrode. To assure sufficient voltage for the stimulus, a charging circuit 58 boosts the source voltage used within the apparatus, as supplied by a single battery, to a sufficient voltage level to provide an adequate electrical stimulus. Battery voltage is preferably boosted by means of a charge pumping arrangement within the charging circuit 58. The timer 60 provides numerous functions at the core of the embodied apparatus circuitry. For example, timer 60 generates timing signals for the charging circuit and measures the time that elapses between each generated stimulus pulse and each attendant response which is detected. The charging circuit 58 provides a signal to the timer 60 when the charging output has reached a sufficient voltage level. The timer 60 subsequently triggers the stimulus pulse from the stimulator 56. Upon triggering the stimulus pulse the timer is reset to a known state (preferably zero) and begins counting upward. The response is monitored along the nerve pathway by electrode input connection 62 comprising a positive electrode input 64*a*, a neutral input 64*b*, and a negative electrode input 64*c*. Positive 64*a* and negative 64*c* inputs are connected to wiring harness 30 (and recording electrode rings 28*a*, 28*b*). The neutral for the recording electrode is in electrical contact with the exterior of the apparatus case, or a portion thereof, to provide a neutral reference (a ground) on the hand of the patient so as to improve the signal to noise ratio for the diagnostic testing. The signal received between the positive and negative electrode inputs 64*a*, 64*c*, are amplified by pre-amp 66 to generate a signal which is then filtered by filter 68. A peak detector 70 receives the filtered signal and generates an output to timer 60 when the peak of the response to the stimulus pulse arrives. The peak response of the incoming signal provides a repeatable position within the response from which to measure the response timing. Using a peak detector provides additional noise immunity in relation to using a fixed threshold as the characteristic of the incoming signal determines the detection and is less prone to false triggering by noise within the signal. The response signal from the peak detector 70 is received within the timer as a load signal wherein the count value is loaded to a display driver 72 and visually indicated on display 74. The timer then continues counting such that at a predetermined count a subsequent stimulus pulse is generated, whereas timing of a subsequent interval commences.

Figure 4:
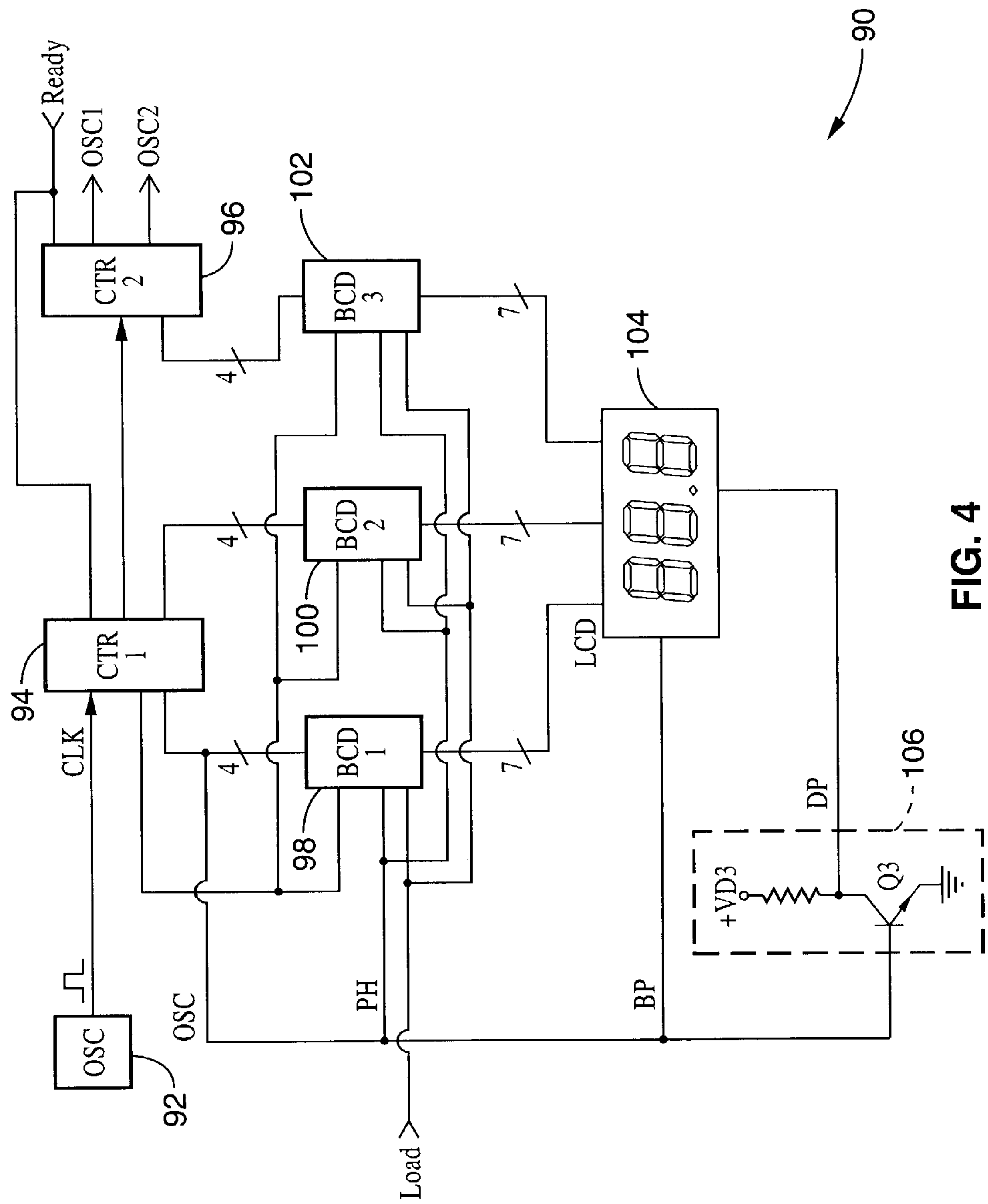
FIG. 4 is a schematic of the display, driver circuits, and latency measurement circuitry according to an aspect of the present invention.

Referring to FIG. 4, an embodiment of circuitry 90 implementing the timer and display elements previously described is shown as a simplified schematic of integrated circuits and signal routing. An oscillator 92 provides a signal at a predetermined frequency as the clock to a counter 94, herein exemplified as a dual binary-coded-decimal (BCD) counter having a first decade whose output cascades to a second decade counter. The output from the second decade counter within counter 94 is received by a counter 96, exemplified as another dual binary-coded-decimal (BCD) counter. In combination, the counters provide four decimal decades, although it will be appreciated that a variety of counter depths can be accordingly supported. The BCD outputs of three of the counter stages are received by display driver circuits 98, 100, 102, which are exemplified as three BCD to seven-segment liquid crystal display (LCD) driver chips. The drivers in turn provide the segment drives for a three-digit LCD display 104. The counters 94, 96, in addition to providing for the measurement of the nerve sensory latency periods, provide outputs used for timing of the LCD backplane signal, signals used for driving the charge pump, and a signal for triggering the pulse from the stimulator circuit. The backplane of the LCD is driven by a clock derived from an intermediate counter output which is also received as a phase signal for the drivers so that the segments may be driven in opposite phase of the backplane. In addition, a fixed decimal point within the LCD is shown being driven by a transistor inverter 106 coupled to the backplane signal. As the stimulator pulse is generated, the counters 94, 96 are reset to zero and then begin counting up from zero. During this time, the display drivers 98, 100, 102, contain a latched BCD value from a previously recorded measurement which is displayed on the LCD 104. A LOAD signal is generated upon arrival of the peak response of the stimulator pulse at the recording electrode. The LOAD signal is received by the drivers whereupon the current BCD count of the counters is loaded into the drivers 98, 100, 102, which updates the display 104. After receipt of the LOAD signal, the counters continue to count up until a high-order bit of the counter goes active to trigger a subsequent stimulus pulse and reset the counters for timing another nerve latency interval.

Figure 5:
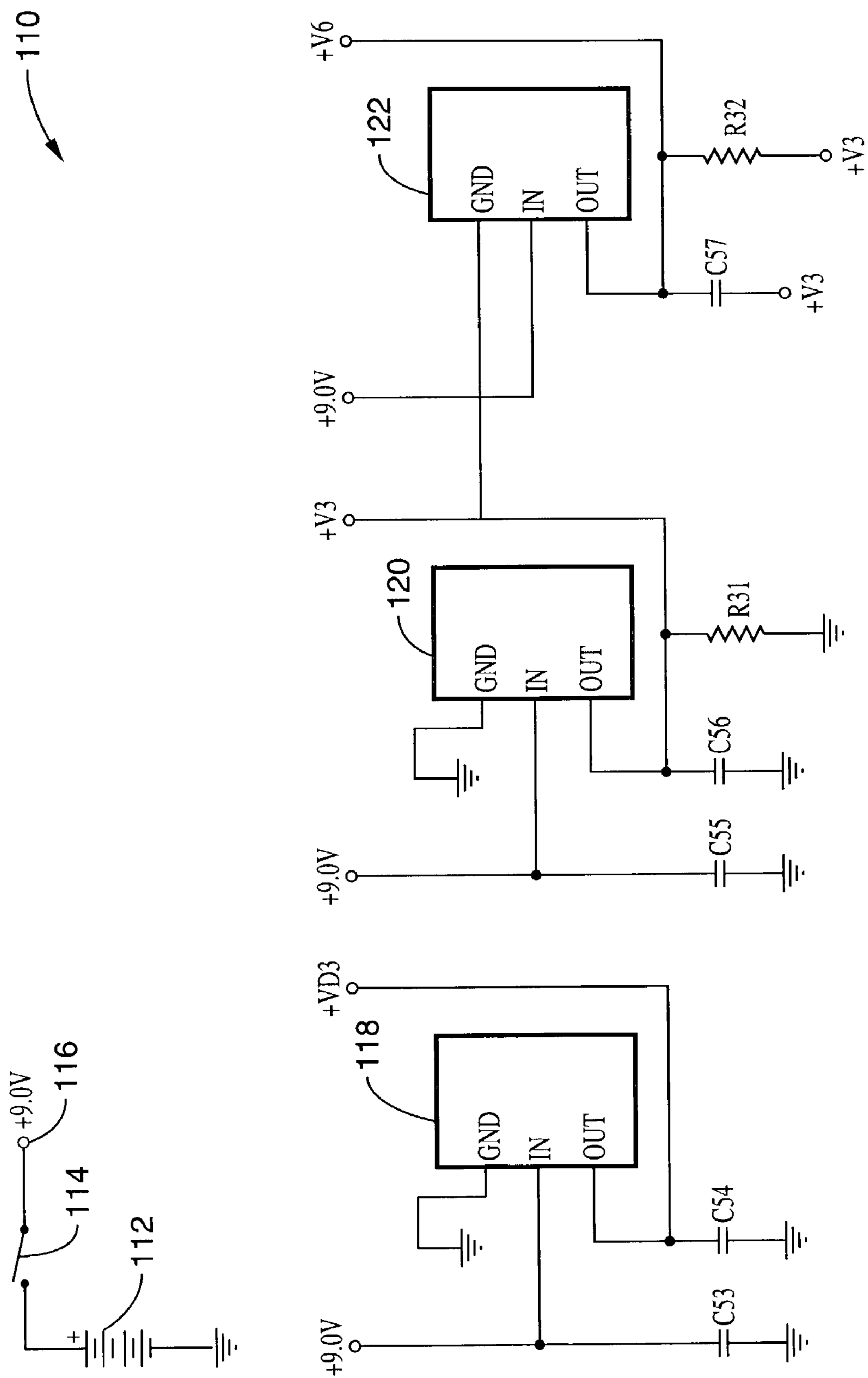
FIG. 5 is a schematic of the power supply circuit according to an aspect of the present invention.

FIG. 5 shows an embodiment of the power source 110 for the apparatus. Power from a battery 112 is controlled by switch 114 to provide power 116 to the regulator circuitry for the apparatus. A set of voltage regulators are also shown which provide the separate isolated voltages necessary within the circuit. Regulator 118 provides voltage VD3 of approximately three-volts, while regulator 120 provides V3 of approximately three-volts with which the three-volt output of regulator 122 is summed to provide V6 a six-volt output. Regulators 120 and 122 thereby provide a split supply for the op-amps with a positive and negative three volts in reference to the center voltage V3.

Figure 6:
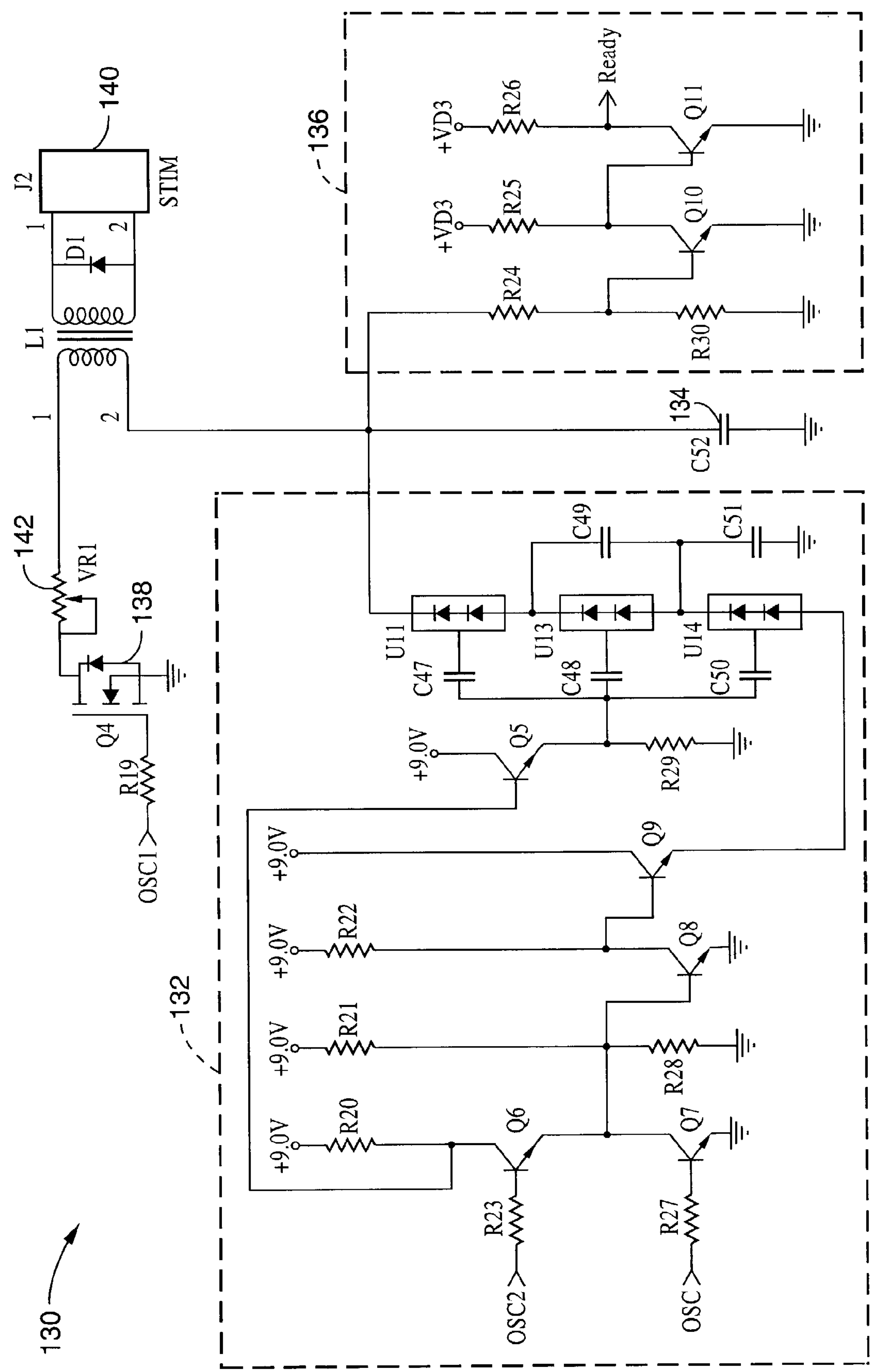
FIG. 6 is a schematic of the stimulus circuit according to an aspect of the present invention.

FIG. 6 shows an embodiment of the stimulator and charge-pump circuitry 130 according to the invention. The charge pump boosts the achievable output voltage by stepping up the battery voltage by a process of adding amounts of charge during successive time intervals to thereby “pump up” the voltage on a capacitor. This charge-pump circuit 132 receives two oscillator signals OSC and OSC2 to drive the pumping phases wherein voltages are essentially “stacked” onto output capacitor 134 in which the stimulus charge is built-up. When the output capacitor reaches a sufficiently high charge level, a sense circuit 136 generates a READY signal. The timer triggers the stimulus pulse by a signal OSC1 to a switching device 138 which discharges the voltage on capacitor 134 as a current pulse through transformer L1. The voltage from capacitor 134 is thereby stepped-up to further increase the output voltage. Preferably, the output voltage of the stimulator can be set to a sufficiently high voltage to allow for proper conduction under the given conditions. Within the exemplified embodiment, transformer L1 has a turns ratio of 1:10 which provides for a maximum stimulus output voltage around 200 VDC in the illustrated circuit. The width of the stimulus pulse delivered through the transformer is preferably about 0.5 milliseconds. The output of transformer L1 is clamped by protection diode D1 and is output on the electrodes of the stimulus probe attached to connector 140 to induce a current across the electrodes. The switching device 138 is herein exemplified as a high-voltage protected MOS FET transistor. The amplitude of the stimulus pulse is regulated by a variable resistor 142 which provides the optional pulse amplitude control 38 as shown in FIG. 1 and FIG. 2.

Figure 7:
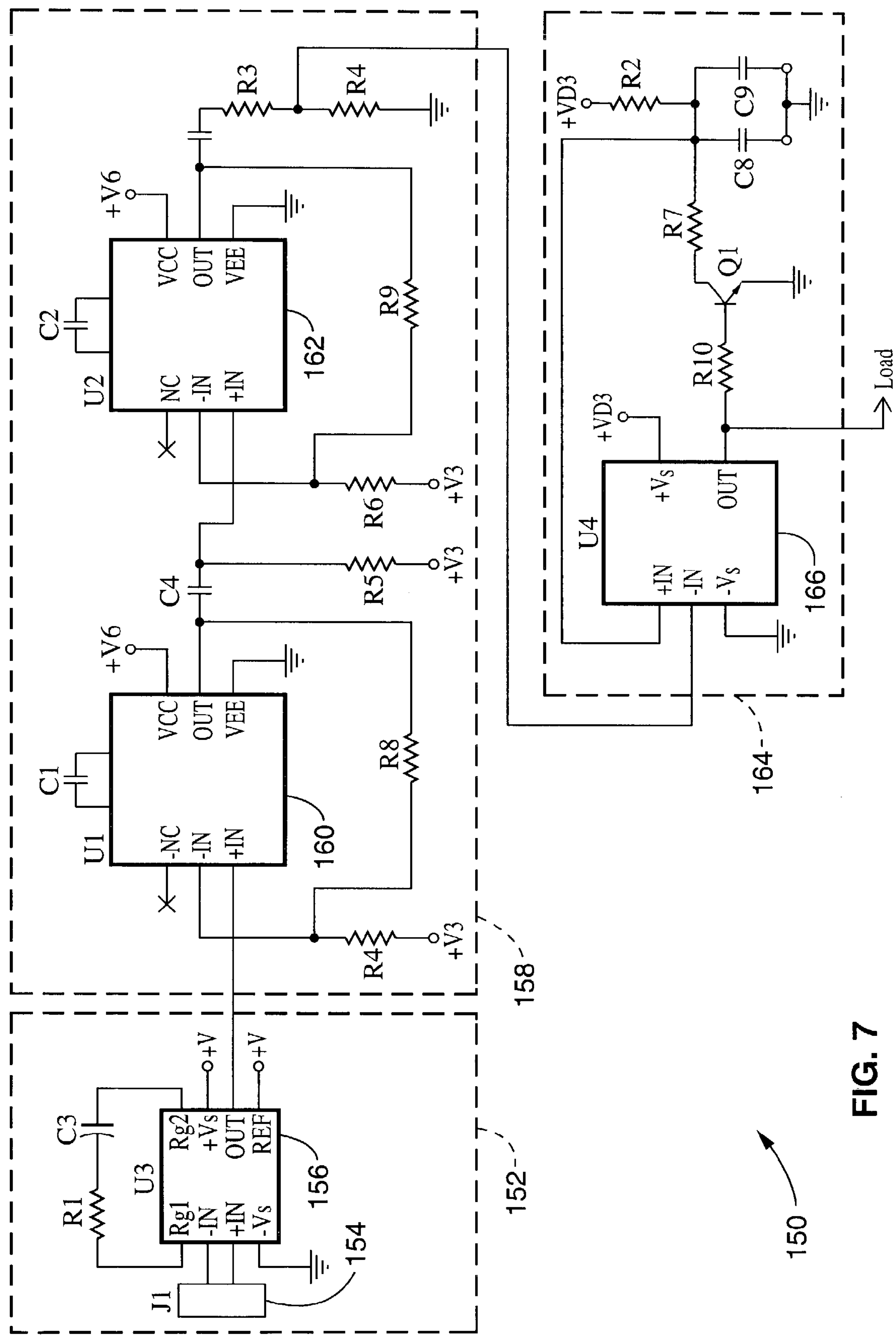
FIG. 7 is a schematic of the response sensing circuit according to an aspect of the present invention.

FIG. 7 shows an embodiment of response detection circuitry 150 for detecting the electrical response which has traversed along a nerve pathway as a result of the stimulus signal from the stimulator. A gain stage 152 contains a connector 154 for connecting with the recording electrode, the signal from which is amplified by op-amp 156. A second stage 158 primarily provides filtering of unwanted noise components from the signal and comprises two op-amps 160 and 162. A third stage 164 provides a signal peak-detector for the circuit comprising an op-amp 166 and a capacitive storage element containing C8 and C9 within the feedback loop for storing a charge voltage to which the signal is compared. Upon peak detection, the op-amp 166 generates a LOAD signal which is used for loading the BCD count value from the counters into the display drivers while it additionally resets the charge element within the feedback loop in preparation for the next stimulus/response cycle.

It will be appreciated that the above description is for the circuitry of a single embodiment for the self-diagnostic analysis apparatus of the present invention and that numerous variations may be derived by one of ordinary skill in the art without departing from the inventive teachings.

Accordingly, it will be seen that this invention provides an apparatus for self-diagnostic evaluation of nerve sensory latency such as that which is characteristic of carpal tunnel syndrome. The apparatus has been developed to allow the user to conduct the measurements on themselves with a single free hand. Furthermore, the apparatus has been designed with a single-battery power source to minimize size weight and cost, and the circuitry within the apparatus developed for simplicity and low power consumption so that the units may be mass-produced for wide distribution. It will be appreciated that the illustrated schematics were provided by way of example and that the numerous variations will be obvious to one skilled in the art without departing from the inventive teachings.

Although the description above contains many specificities, these should not be construed as limiting the scope of the invention but as merely providing illustrations of some of the presently preferred embodiments of this invention. Thus the scope of this invention should be determined by the appended claims and their legal equivalents. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean “one and only one” unless explicitly so stated, but rather “one or more.” All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of. 35 U.S.C. 112, sixth paragraph, unless the element is expressly recited using the phrase “means for.”

What is claimed is:

1. An apparatus for self-diagnostic evaluation of nerve sensory latency, such as that which is symptomatic of carpal tunnel syndrome, comprising:

(a) a power source;

(b) a stimulator circuit configured for coupling to a first electrode at a first contact position on the skin of the user and for generating an electrical pulse from said power source at a selectable time;

(c) a sense circuit configured for coupling to a second electrode at a second contact position on the skin of the user and for detecting the nerve response associated with the electrical pulse generated by the stimulator circuit as it arrives proximal to said second contact position;

(d) a timer circuit configured for recording the time interval between the generation of the electrical pulse by the stimulator circuit and the arrival of the pulse response within the sense circuit; and (e) a display circuit operatively coupled to said timer and configured for displaying the time interval as recorded by the timer circuit.

2. An apparatus as recited in claim 1, wherein said power source comprises a single battery.

3. An apparatus as recited in claim 1, wherein during the period of time that the power source is activated, the stimulator circuit generates a continuing series of electrical stimulus pulses.

4. An apparatus as recited in claim 1, further comprising voltage regulation circuitry coupled to said power source and configured for generating intermediate voltages for use within said circuits.

5. An apparatus as recited in claim 1, further comprising a peak detector within the sense circuit configured to detect a peak of an associated pulse response signal whereby noise immunity is improved over sensing performed with a fixed threshold.

6. An apparatus as recited in claim 1, wherein the stimulator circuit converts voltage provided by the power source to a sufficiently high voltage that said pulse can be properly coupled to the nerves within a nearby nerve pathway and registered by the sense circuit.

7. An apparatus as recited in claim 1, further comprising a charge pump circuit for incrementally converting the voltage provided by the power source to a high-voltage as stored on an output capacitor.

8. An apparatus as recited in claim 7, further comprising a transformer for converting the voltage which is stored on the output capacitor to a maximum peak voltage of around 200 volts.

9. An apparatus as recited in claim 1, wherein the timer circuit comprises a counter circuit configured to receive periodic pulses from an oscillator which modify a count value, the count value being loaded into the display in response to detecting the arrival of the stimulus pulse at the sensor circuit, and said counter being reset upon generation of a subsequent stimulus pulse.

10. An apparatus as recited in claim 9, wherein the display circuit comprises a liquid crystal display driven by an output stage of the counter circuit that also provides a phase signal utilized within the driver circuit for display segment driving.

11. An apparatus as recited in claim 9, wherein transition of a high-order intermediate output stage of the counter circuit provides a trigger signal which activates the stimulator circuit.

12. An apparatus as recited in claim 9, wherein an intermediate output stage of the counter circuit provides a second oscillator signal for the stimulator circuit, that in combination with the periodic pulses from the oscillator circuit provides the signal phases for operating a charge pump within the stimulator circuit so as to create a voltage of sufficient amplitude to properly drive the output of the stimulator upon being triggered.

* * * * *